(12) United States Patent
Shaz et al.

(10) Patent No.: US 8,968,993 B2
(45) Date of Patent: Mar. 3, 2015

(54) METHOD OF BLOOD POOLING AND STORAGE

(71) Applicant: New York Blood Center, Inc., New York, NY (US)

(72) Inventors: Beth H. Shaz, New York, NY (US); Christopher D. Hillyer, New York, NY (US)

(73) Assignee: The New York Blood Center, Inc., New York, NY (US)

( * ) Notice: Subject to any disclaimer, the term of this patent is extended or adjusted under 35 U.S.C. 154(b) by 0 days.

(21) Appl. No.: 13/944,674

(22) Filed: Jul. 17, 2013

(65) Prior Publication Data

US 2013/0302780 A1 Nov. 14, 2013

Related U.S. Application Data

(63) Continuation of application No. 13/306,759, filed on Nov. 29, 2011, now Pat. No. 8,512,942.

(60) Provisional application No. 61/417,771, filed on Nov. 29, 2010.

(51) Int. Cl.
*A01N 1/02* (2006.01)

(52) U.S. Cl.
USPC .................................................. 435/2

(58) Field of Classification Search
USPC .................................. 435/2; 210/806; 436/520
IPC .......... A61K 35/14; A61M 2202/20,2202/0429; C12N 5/0641
See application file for complete search history.

(56) References Cited

U.S. PATENT DOCUMENTS

| | | | |
|---|---|---|---|
| 4,540,573 A | 9/1985 | Neurath et al. | |
| 4,789,545 A | 12/1988 | Woods et al. | |
| 5,120,649 A | 6/1992 | Horowitz et al. | |
| 5,232,844 A | 8/1993 | Horowitz et al. | |
| 5,541,294 A | 7/1996 | Horowitz et al. | |
| 5,637,451 A | 6/1997 | Ben-Hur et al. | |
| 5,658,722 A | 8/1997 | Margolis-Nunno et al. | |
| 5,670,060 A * | 9/1997 | Matkovich et al. | 210/767 |
| 5,712,086 A | 1/1998 | Horowitz et al. | |
| 5,981,163 A | 11/1999 | Horowitz et al. | |
| 6,077,659 A | 6/2000 | Ben-Hur et al. | |
| 6,090,599 A | 7/2000 | Ben-Hur | |
| 6,136,586 A | 10/2000 | Budowsky et al. | |
| 6,214,534 B1 | 4/2001 | Horowitz et al. | |
| 6,294,361 B1 | 9/2001 | Horowitz et al. | |
| 6,413,714 B1 | 7/2002 | Margolis-Nunno et al. | |
| 6,548,242 B2 | 4/2003 | Horowitz et al. | |
| 6,730,230 B2 | 5/2004 | Cook et al. | |
| 8,512,942 B2 * | 8/2013 | Shaz et al. | 435/2 |
| 2002/0192632 A1 * | 12/2002 | Hei et al. | 435/2 |
| 2004/0236263 A1 | 11/2004 | Van Waeg et al. | |
| 2008/0050275 A1 * | 2/2008 | Bischof et al. | 422/32 |
| 2011/0230369 A1 | 9/2011 | Buffet et al. | |
| 2012/0111807 A1 | 5/2012 | Hilyer et al. | |
| 2012/0252001 A1 | 10/2012 | Shaz | |
| 2013/0004937 A1 | 1/2013 | Yoshida et al. | |

FOREIGN PATENT DOCUMENTS

| | | |
|---|---|---|
| WO | 93/25295 | 12/1993 |
| WO | 96/39026 | 12/1996 |
| WO | 98/41087 | 9/1998 |
| WO | WO 98/41087 * | 9/1998 |
| WO | 98/46073 | 10/1998 |
| WO | 00/32542 | 6/2000 |
| WO | 00/74483 | 12/2000 |
| WO | 03/049784 | 6/2003 |

OTHER PUBLICATIONS

Fujihara M. et al. Prestorage Leucofiltration Prevents the Accumulation of MMP-9 in Red Cell Concentrates Stored in Mannitol Adenine Phosphate Medium. Vox Sanguinis 89(2)114-115, Aug. 2005.*
Gilson C. et al. A Novel Mouse Model of RBC Storage and Post-transfusion In vivo Survival. Transfusion 49(8)1546-1553, Aug. 2009.*
Beutler et al., The definition of anemia: what is the lower limit of normal of the blood hemoglobin concentration? Blood, 107(5): 1747-1750 (2006).
Fujihara et al., Prestorage leucofiltration prevents the accumulation of matrix metalloproteinase-9 in red cell concentrates stored in mannitol-adenine-phosphate medium. Vox Sanguinis 89(2): 114-115 (2005).
International Search report for International Application No. PCT/US2011/062460 mailed Aug. 30, 2012.
Kor DJ et al., Red blood cell storage lesion. Bos J. Basic Med. Sci. 9(SUPP)S21-S27 (2009).
Zhang et al., Cell Couter, Blood. Encyclopedia of Medical Devices and Instrumentation, Second Edition, p. 81-90 (2006).
Zimmerman et al., Influence of late irradiation on the in vitro RBC storage variables of leucoreduced RBCs in SAGM additive solution. Vox Sanguinis 100(3): 279-284 (2010).
Zimmerman et al., Influence of prestorage leudoreduction and subsequent irradiation on in vitro red blood cell (RBC) storage variables of RBCs in additive solution saline-adenine-glucose-mannitol. Transfusion 49(1): 75-80 (2009).
Deplaine et al., The sensing of poorly deformable red blood cells by the human spleen can be mimicked in vitro. Blood, vol. 117, No. 8, e88-e95 (2011).

(Continued)

*Primary Examiner* — Ralph Gitomer
(74) *Attorney, Agent, or Firm* — K&L Gates LLP; Louis C. Cullman; Michelle Glasky Bergman

(57) ABSTRACT

The disclosure provides methods of making a cell-containing product having a uniform amount of cells therein. The method comprises pooling red blood cells from a plurality of blood units, and inactivating any pathogen contained therein. A storage solution added to the cellular component results in a cell-containing product that is essentially pathogen and white blood cell free and has an extended shelf life of about 42 to about 100 days. The cell-containing product is further divided into units which comprise a uniform dose of RBCs per unit.

7 Claims, 1 Drawing Sheet

(56) References Cited

OTHER PUBLICATIONS

Extended European Search Report mailed on Apr. 1, 2014 for European Application 11845230.9.

Hod et al., Transfusion of human volunteers with older, stored red blood cells produces extravascular hemolysis and circulating non-transferrin-bound iron. Blood, 118(25): 6675-6682 (2011).

Hod et al., Harmful effects of transfusion of older stored red blood cells: iron and inflammation. Transfusion, 51(4): 881-885 (2011).

Hod et al., Use of mouse models to study the mechanisms and consequences of RBC clearance. Vox Sang, 99(2): 99-111 (2010).

Hod et al., Transfusion of red blood cells after prolonged storage produces harmful effects that mediated by iron and inflammation. Blood, 115(21): 4284-4292 (2010).

Hendrickson et al., Rapid clearance of transfused murine red blood cells is associated with recipient cytokine storm and enhanaced alloimmunogenicity. Transfusion, 51(11): 2445-2454 (2011).

Hess, J.R., for the biomedical excellence for safer transfusion (BEST Collaborative). Scientific problems in the regulation of red blood cell products. Transfusion, epub (2012).

Prince et al., Evaluation of the effect of betapropiolactone/ultraviolet irradiation (BPL/UV) treatment of source plasma on hepatitis transmission by Factor IX complex in chimpanzees. Journal of the International Society on Thrombosis and Haemostatis, 44(3): 138-142 (1980).

* cited by examiner

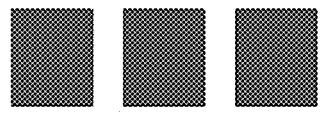
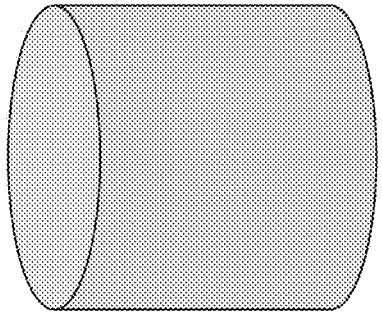
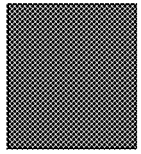

METHOD OF BLOOD POOLING AND STORAGE

CROSS-REFERENCE TO RELATED APPLICATIONS

The present application is a continuation of U.S. patent application Ser. No. 13/306,759, filed Nov. 29, 2011, now U.S. Pat. No. 8,512,942, which claims the benefit under 35 U.S.C. §119(e) to U.S. Provisional Application 61/417,771 filed Nov. 29, 2010, the entire contents of each of which are incorporated by reference herein.

BACKGROUND

A single donation of whole blood can supply red blood cell (RBCs), platelet, and plasma products, which can potentially benefit three different patients. Stored RBCs currently suffer certain disadvantages. The lifespan of stored RBCs is 42 days, which given the fluctuation of supply and demand for RBCs, can lead to dangerous shortages in times of unexpected need. RBCs can also harbor pathogens that can endanger the recipient if the pathogen is transmitted via transfusion. In addition, an individual donates each unit of blood collected which is fractionated and stored separately resulting in a great degree of variance in the amount of RBCs collected and stored in each unit. As a result, the concentration and volume of RBCs varies from unit to unit and thus the number of RBCs administered to a given recipient is variable.

Accordingly, a pathogen-free RBC product that has an increased lifespan and provides a uniform amount of RBCs per unit would be highly desirable.

BRIEF SUMMARY

The disclosure provides a cell-containing product and methods for making the cell-containing product. In one embodiment, a method for preparing a cell-containing product is provided comprising a) obtaining a plurality of whole blood units, b) separating a desired cell component from the blood units, c) leukoreducing the whole blood or cell component, d) pooling the desired cell component, e) treating the cell component to inactivate one or more pathogens, and f) adding a storage solution to the cell component, wherein the cell component in the storage solution provides a cell-containing product having a storage life of about 42 to about 100 days. In an alternate embodiment, the blood can be fractionated prior to pooling. In one embodiment, the cell-containing product is a red blood cell-containing product. In another embodiment, the method comprises segregating the cell component by blood type prior to the pooling step. In another embodiment, the cell component is divided into a plurality of units, each unit having a uniform dose of the cell component.

In another embodiment, a cell-containing product is obtained by a method comprising: a) obtaining a plurality of whole blood units, b) separating a desired cell component from the obtained blood, c) leukoreducing the whole blood or cell component; d) pooling the desired cell components, e) treating the separated cell component to inactivate one or more pathogens, and f) adding a storage solution to the cell component, wherein the cell component in the storage solution provides a cell-containing product having a storage life of about 42 to about 100 days.

In yet another embodiment, a method of making a plurality of units of RBCs is disclosed comprising a) pooling leukoreduced RBCs from a plurality of blood units, b) treating the RBCs to inactivate one or more pathogens, and c) separating RBCs into a plurality of units comprising a uniform dose of RBCs. In another embodiment, the method comprises segregating the cell component by blood type prior to the pooling step and pooling only units having the same blood type.

In another embodiment, a cell-containing product is disclosed comprising a uniform amount of RBCs obtained by a method comprising the steps of: a) obtaining a plurality of whole blood units b) separating the RBCs from the plurality of blood units, c) leukoreducing the whole blood or RBCs, d) pooling the separated RBCs, d) treating the RBCs to inactivate one or more pathogens, and e) adding a storage solution to the RBCs, wherein the RBCs in the storage solution provides a cell-containing product, and e) dividing the cell-containing product into a plurality of units comprising a uniform dose of RBCs.

In one embodiment, the blood unit comprises a unit of whole blood or RBCs obtained by apheresis.

In another embodiment, the storage solution comprises at least one material selected from the group consisting of adenine, glucose, phosphate, mannitol, guanosine, and a combination thereof.

In yet another embodiment, the treating step inactivates one or more pathogens without damaging the structure or function of the cell component. In another embodiment, the one or more pathogens are selected from the group consisting of viruses, bacteria, fungi, prions, parasites, and combinations thereof. In another embodiment, the one or more pathogens are inactivated by at least one method selected from the group consisting of irradiation, solvent and detergent, magnetophoresis, immunomagnetic bead technology, and a combination thereof. In another embodiment, the method further comprises a step of inactivating residual white blood cells in the pooled RBC component.

In another embodiment, each of the pooled RBC components is of the same blood type. In still another embodiment, the blood type is selected from ABO, Rh, and a combination thereof.

In another embodiment, the cell containing product is divided into one or more units before or after adding the storage solution. The uniform dose of RBCs is a uniform number of RBCs per unit or a uniform hemoglobin concentration. In certain embodiments, the uniform dose comprises a RBC dose of 1–5×10$^{12}$ RBCs/unit, or 2–3×10$^{12}$ RBCs/unit. In other embodiments, the uniform dose comprises a hemoglobin concentration of about 20-80 g/unit, or about 50 g/unit.

BRIEF DESCRIPTION OF THE DRAWINGS

FIG. 1 is a schematic of the steps of a blood pooling, pathogen inactivation, and blood storage method in accordance with an embodiment of the disclosure.

DETAILED DESCRIPTION

The disclosure provides a method for obtaining a pathogen free pharmaceutical grade red blood cell (RBC) product that contains a uniform unit dose of RBCs, presents a reduced risk of inducing adverse effects in the recipient, and has an increased storage life. A further advantage of administering the unit of RBCs obtained according to the disclose methods is the mitigation of adverse events such as transfusion associated graft vs. host disease, disease transmission, transfusion related immunomodulation (potentially resulting in nosocomial infection, multiorgan failure) and transfusion associated lung injury.

In one embodiment, a method of making a cell containing component is provided that comprises a) obtaining a plurality of whole blood units, b) separating a desired cell component from the blood units, c) leukoreducing the whole blood or the desired cell component; d) pooling the desired cell components from the blood units, e) treating the cell component to inactivate one or more pathogens, and f) adding a storage solution to the cell component. In certain embodiments, the step of inactivating one or more pathogens can take place prior to separating the desired cell component from the pooled blood.

Blood units can be obtained from one donor or a plurality of donors according to methods known to persons of ordinary skill in the art. In certain embodiments, the blood is segregated according to one or more blood type group (ABO, RhD, Kell, Duffy, etc) prior to pooling. In certain embodiments, the pooled RBCs or blood units have the same blood type of at least one blood group. The blood units can be typed for one, two or more blood groups and pooled based on the one, two or more blood groups. In certain embodiments, the pooled blood units each have the same ABO blood type and the same Rh blood type. In another embodiment, the pooled blood units each have the same ABO type but differ in Rh blood type. The donors are typically mammals, such as humans. The donors can be any gender, age, race or ethnicity. In another embodiment, RBCs obtained from whole blood or from apheresis donors.

In one embodiment, the obtained blood units are fractionated and an RBC fraction is obtained. In addition to, or in lieu of the RBCs, fractionated platelets and/or plasma can be separated and pooled. The fractionated RBCs are pooled; that is RBCs from a plurality of blood units are collected and stored together for further processing.

In certain embodiments, the blood cell product is a homogenous RBC product that is obtained by fractionation or other known separation means. Blood and erythrocyte fractionation relies on the unique structure of the RBCs to separate them from plasma and other elements in the blood. Fractionation of whole blood into its constituents is an established technique, well known in the art. Typically, whole blood is centrifuged with or without an isotonic buffer at low speed for a short period of time. Although the speed of centrifugation can vary, centrifugation at a range of about 600 to about 3900 rpm for about 5 to about 20 minutes at about −10° C. to about 20° C. is usually sufficient to separate the RBCs from the other components. In one embodiment, for example, whole blood stored at 4° C. is centrifuged at 2000 rpm for about 20 minutes. The RBC concentrate is diluted 2-fold with a phosphate buffered saline. The blood fractionation step can occur before or after leukoreduction and/or the pathogen and white blood cell (WBC) inactivation and removal step.

In another embodiment, the blood components are separated using a blood component separation system, such as the system described in co-pending U.S. patent application Ser. No. 13/291,822 filed on Nov. 8, 2011. Other blood component separation systems are known in the art and any system which produces a cell-containing product are suitable for use with the methods disclosed herein.

The separated blood components are pooled in a vat or container large enough to contain the blood components and any additional materials necessary (storage solution, additives, radiation sensitizers, photoquenchers, etc.). The vat or storage container maintains the blood components and additives in a sterile environment and allows the addition or removal or material without exposure to a non-sterile environment.

Any number of units of leukoreduced blood, or RBCs, can be pooled. In certain embodiments, 10-100 units of leukoreduced whole blood or RBCs are pooled.

The pooled blood, or RBC units are then treated to inactivate any pathogens present in the donated blood units. A variety of pathogens can be inactivated with the methods disclosed herein. In addition, residual WBCs not removed during leukoreduction, which can transmit pathogens contained within and also invoke immunogenic reactions, can be removed and/or inactivated. Removal of residual WBCs from the pooled blood can be achieved by any known means of leukoreduction including, but not limited to, leukoreduction filters, gradient centrifugation, etc. (see, for example, LEUKOTRAP®, Pall Corp)

Pathogen and WBC inactivation, in accordance with the methods disclosed herein, results in an eradication of the infectious agent while preserving the structure and function of the RBCs. That is, greater than 70%, 80%, 90% or even 95% of the RBCs are considered viable following pathogen inactivation, which is indicative of a high level of retention of intact cell function and structure. RBC viability can be assessed by visual inspection of the sample and/or by determining the percent hemolysis in a stored unit. Such analyses are routine in the art and can be conducted by the tetramethylbenzidiene (TMB) method or using a hematology analyzer (e.g., Beckman Coulter AcT). RBC viability corresponds to post-transfusion in vivo circulatory survival time. The RBCs described herein have a circulatory survival time of about 110 days in vivo.

One or more methods of pathogen inactivation can be used in accordance with the disclosed methods. Via the inactivation procedures disclosed herein, essentially all pathogens in the whole blood or RBC component are reduced. Methods for determining infectivity levels are known to persons of ordinary skill in the art (see for example, *Thrombosis and Hemostasis*, 44:138-142, 1980). In accordance with the disclosed methods, at least $10^4$ infectious units of pathogen are inactivated. In certain embodiments, at least $10^5$ infection units or at least $10^6$ infectious units of pathogen are inactivated. Restated, inactivation of pathogen is obtained to the extent of at least "4 logs", and alternatively, greater than 5 logs or greater than 6 logs, such that pathogen in the sample is reduced to the extent determined by infectivity studies where that pathogen is present in the untreated sample in such a concentration that even after dilution to $10^4$, $10^5$, or $10^6$, pathogen activity can be measured. For the purposes of this disclosure, the terms "inactivate" and "reduce" both refer to a multiple log reduction in the number of viable pathogens in the whole blood or RBC component.

In certain embodiments, a pathogen in the blood cell product is inactivated using irradiation. The term "irradiation" refers to any form of radiation conventionally used to inactivate cells or pathogens (WBCs, viruses, parasites, bacteria, or other pathogenic organisms) either alone or in combination with some other agent or condition. Non-limiting examples of irradiation include ultraviolet (UVA, UVB, UVC), gamma-irradiation, X-irradiation, and visible light. Monochromatic light in the range of about 660-700 nm is included in this definition as well.

In one embodiment, an effective amount of irradiation is applied in the presence of a mixture of (a) compound that quenches photodynamic type I reactions and a compound that quenches type II photodynamic reactions, or (b) a bifunctional compound that quenches both types of photodynamic reactions. A typical radiation fluence range is 5-100 J/cm$^2$ or 50-100 J/cm$^2$ for UVA, 0.02-2 J/cm$^2$ or 0.05-0.2 J/cm$^2$ for UVC, and 1-40 kGy for gamma-irradiation. Quenchers scavenge type I and or II reactions and thereby provide protection to the RBCs. Suitable quenchers are any known to react with both free radicals (type I quenchers) or reactive forms of oxygen (type II quenchers). Representative quenchers include unsaturated fatty acids, reduced sugars, cholesterol indole derivatives, azides (e.g., sodium azide), tryptophan, polyhydric alcohols (e.g., glycerol, mannitol), thiols (e.g., glutathione), superoxide dismutase, flavonoids (e.g., quercetin and rutin), amino acids, DABCO, vitamins, and combinations thereof.

The irradiation process can be carried out over a temperature range of about 0° C. to about 42° C. In certain embodiments, the temperature is about 20° C. to about 27° C., or about 20° C. to about 25° C. The pathogen inactivation process is carried out for a time less than 24 hours, and in certain embodiments, less than 10, less than 8, or less than 4 hours. In certain embodiments, irradiation is carried out for about 1 minute to about 240 minutes or, alternately, about 5 minutes to about 120 minutes. During the inactivation process, the RBC suspension can be maintained at a pH range of about 6.5-8, preferably 7.2-7.6.

The irradiation process can occur in the presence of one or more radiation sensitizers. Suitable radiation sensitizers include, but are not limited to, phthalocyanines, purpurins, and other molecules resembling porphyrins, photoactive compounds excited by UV light (e.g., psoralen, 8-methoxypsoralen, 4'-aminomethyl-4,5',8-trimethylpsoralen, bergapten, angelicin), dyes that absorb light in the visible spectrum (e.g., pypericin, methylene blue, eosin, fluoresceins, flavins), dyes that absorb X-irradiation (e.g., brominated psoralen, brominated hematoporphyrin, iodinated phthalocyanine), and combinations thereof. The use of irradiation sensitizers is known in the art and is described in, for example, U.S. Pat. Nos. 5,120,649, 5,232,844, and 6,548,242, the disclosures of which are incorporated herein by reference.

Following pathogen inactivation with photoreactive compounds, the photoreactive compound can be removed by any known means, such as, centrifugation, washing, dialysis, and/or adsorption onto hydrophobic matrices.

In lieu of, or in addition to, the above described pathogen inactivation methods, a solvent-detergent method can be used to inactivate pathogens in blood. This method is described, for example, in U.S. Pat. No. 4,540,573, which is incorporated herein by reference. Organic solvents can be combined with anionic or nonionic detergents to kill pathogens and preserve desirable cellular components. For instance, an organic solvent, such as tri(n-butyl)phosphate combined with nonionic detergents such as TWEEN 80 or TRITON X-100. Alternately, a nonanionic detergent, alcohol, ether, or mixtures thereof can be used. In one embodiment, an RBC containing solution can be contacted with a dialkylphosphate or a trialkylphosphate having alkyl groups that contain 1 to 10 carbon atoms, preferably 2-10 carbon atoms. Mixture of such compounds can be used as well as phosphates having alkyl groups of different length chains, for example, ethyl di(n-butyl) phosphate. Mixtures of di- and trialkylphosphates can be utilized in accordance with the disclosure. Di- or trialkylphosphates can be used in an amount of about 0.01 mg/ml to about 100 mg/ml, preferably about 0.1 mg/ml to about 10 mg/ml. Treatment can occur at a temperature of about −5° C. to about 70° C. In certain embodiments, treatment can occur at a temperature between about 0° C. and about 60° C. Treatment can occur for about 1 hour to about 24 hours. Following pathogen inactivation of the RBC containing solution, the di-, trialkylphosphate, or nonionic detergent can be removed by any known means such as extraction (see U.S. Pat. No. 4,789,545), diafiltration with ether insoluble (e.g., TEFLON microporous membranes), adsorption using chromatographic or affinity chromagraphic supports, and/or precipitation.

Wetting agents can be used in conjunction with the di- and trialkylphosphates to enhance the contact of the pathogen with the di- and trialkylphosphates. In certain embodiments, the wetting agent is a nonionic detergent. Detergents containing polyoxyethylene derivatives of fatty acids, or partial esters of sorbitol anhydrides are suitable. Examples of such detergents include, but are not limited to commercially available products TWEEN 80, TWEEN 20, polysorbate 80, and nonionic oil soluble water detergents such as oxyethylated alkylphenol (aka TRITON X100). Zwitterionic detergents such as N-dodecyl-N,N-dimethyl-2-ammonio-1-ethane sulphonate and its congeners, or non-ionic detergents such as octyl-beta-D-glucopyranoside are also suitable. The amount of wetting agent can be in a range from about 0.001% to about 10%. In certain embodiments, the wetting agent is present in an amount of about 0.01% to about 1.5%.

Other known methods of pathogen inactivation such as heat treatment, pH manipulation, methylene treatment, additional radiation treatments (with or without a chemical agent, such as formaldehyde, cyanines, riboflavin), inactivation and removal with microparticles (see U.S. Pat. No. 6,730,230), magnetophoresis, microdevices utilizing immunomagnetic and microfluidic technology, and/or immunomagnetic beads, can be used.

As stated above, in certain embodiments of the disclosed methods, pathogens in the blood samples are inactivated. A number of blood borne pathogens are known and, if present in a blood sample, can transmit disease to a recipient. Diseases such as human immunodeficiency virus (HIV), hepatitis, syphilis, malaria, babesiosis, brucellosis, leptospirosis, arboviral infection, relapsing fever, Creutzfeldt-Jakob disease, human T-lymphotropic virus type I, and viral hemorrhagic fever can be transmitted via blood. Accordingly, the categories of pathogens that can be inactivated using the disclosed methods include, but are not limited to, viruses (including cell-free lipid enveloped viruses, actively replicating cell-associated viruses, non-enveloped viruses, and latent cell-associated viruses), bacteria, fungi, prions, and parasites.

A number of viruses are blood borne and therefore transmittable via transfusion. Non-limiting examples of lipid-coated human viruses include, but are not limited to, vesicular stomatitis virus (VSV), moloney sarcoma virus, Sindvis virus, human immunodeficiency virus (HIV-1, HIV-2), human T-cell lymphotrophic virus-I (HTLV-I), hepatitis B virus, non-A, non-B hepatitis virus (NANB; aka hepatitis C), cytomegalovirus, Epstein Barr, virus, lactate dehydrogenase elevating virus, herpes group viruses, rhabdovirus, leukoviruses, myxoviruses, alphaviruses, arboviruses (group B), paramyxoviruses, arenaviruses, and coronaviruses.

Nonlimiting examples of non-enveloped virus that can be inactivated in accordance with the disclosed methods include parvovirus, polio virus, hepatitis A virus, enteric non-a, non-B hepatitis virus, bacteriophage M13, and satellite adeno-associated virus (AAV).

Bacterial contamination of blood products can cause infection in a recipient. Examples of bacterial infections that can be inactivated in accordance with the methods disclosed herein include *Yersinia pestis, Haemophilus influenzae, Staphylococcus aureus, Neisseria meningitides, Neisseria gonorrhoeae,* and *Streptococcus pyogenes.*

Protozoa can cause a number of infections in humans, including: malaria, amoebiasis, babesiosis, giardiasis, toxoplasmosis, cryptosporidiosis, trichomoniasis, leishmaniasis, trypanosomiasis, and sleeping sickness. The organisms causing these illnesses can be inactivated in accordance with the disclosed methods.

Some fungi can cause disease in humans, including, but not limited to, aspergilloses, candidoses, coccidioidomycosis, cryptococcosis, histoplasmosis, mycetomas, and paracoccidioidomycosis. The fungi leading to these and other infections can be inactivated with the disclosed methods.

Prions are proteinaceous infection particles that cause a number of diseases in mammals. In humans, prions are associated with Creutzfeldt-Jakob disease (i.e., mad cow disease). Prion inactivation can be achieved with the pathogen inactivation methods disclosed herein or by other methods known to persons of ordinary skill in the art.

Before or after addition of a storage solution, a plurality of RBCs units are prepared in which each unit has an approximately uniform dose of RBCs. The pooled RBCs are kept suspended in solution by any known means (mechanical agitation, fluid agitation) in order to maintain the RBCs evenly distributed in solution such that a unit having a uniform dose of RBCs can be prepared. By uniform dose, it is meant that the amount of RBCs, i.e., the number of RBCs per unit, does not vary by more than about 20%, about 15%, about 10% or about 5% from unit to unit. The size of a unit prepared in accordance with the disclosed methods can vary depending on the desired use. That is, the RBCs can be stored in smaller and larger aliquots in order to serve neonatal, pediatric and/or adult populations. In general, RBC units contain at least about $1 \times 10^9$ RBCs/mL, at least about $5 \times 10^9$ RBCs/mL, or at least $1 \times 10^{10}$ RBCs/mL. Alternatively, the uniform dose of RBCs can be $1-5 \times 10^{12}$ RBCs per unit. In additional embodiments, the uniform dose of RBCs can be $2-4 \times 10^{12}$ RBCs per unit or $2-3 \times 10^{12}$ RBCs per unit.

Additionally, a "uniform dose of RBCs" can refer to a uniform hemoglobin concentration and the RBC units can be sized such that they contain a standard or uniform dose of hemoglobin, regardless of number of RBCs. In one embodiment, each unit contains 20-80 grams of hemoglobin, 30-70 grams of hemoglobin, 40-60 grams of hemoglobin, or about 50 grams of hemoglobin per RBC unit.

Following pathogen inactivation, RBCs are stored in a storage solution. The storage solution can be any that preserves 2,3-diphosphoglycerate (DPG) and maintains high adenine triphosphate (ATP) concentrations, minimizes hemolysis (hemolysis <1%), and reduces potassium leak, thereby improving the structure and function of the stored RBCs. RBC storage solutions are known in the art (e.g., ADSOL, Baxter Healthcare, Deerfield Ill.; SAGM [saline-adenine-glucose-mannitol] and PAGGSM [phosphate, adenine, glucose, guanosine, saline and mannitol]). The storage solutions disclosed herein include one or more of adenine, glucose, sodium phosphate, mannitol, dextrose, sodium chloride, sodium citrate, citric acid, and guanosine. In one embodiment, the storage solution comprises adenine, glucose, sodium phosphate, mannitol and guanosine.

RBCs, using known protocols and storage solutions, can be stored for approximately 42 days before administration to a subject, after which time the structure, function and viability of the of the RBCs is compromised. In contrast, using the disclosed methods, the obtained RBC product can be stored for about 42 days to about 100 days, or for about 60 days to about 100 days, or for about 70 days to about 90 days. The units can be stored at a temperature of about 1° C. to about 6° C. Further, in accordance with the disclosed methods, the biochemical changes (loss of 2,3-DPG/ATP, inability to release adequate oxygen, potassium leakage), biomechanical changes (deformation of biconcave disc, impaired movement through microcirculation, hemolysis), and immunologic changes that occur in ex vivo storage of RBCs (collectively referred to as "RBC storage lesion") are reduced. These changes can greatly affect RBC and patient survival post-transfusion and therefore, a reduction in one or more of these parameters can confer significant advantages and increase the success of the RBC transfusion.

The methods disclosed herein can be performed utilizing known equipment and reagents. Any available assortment of collection tubing, collection bags, and storage bags can be used in accordance with the disclosed methods. In certain embodiments, di(2-ethylhexyl) phthalate (DEHP) free tubing, collection, and storage bags are desirable.

The methods disclosed herein are well suited for a variety of settings, including but not limited to, community and other blood banks, military sites, hospitals, and clinics.

Example 1

Approximately 10 to 100 units of RBC are fractionated from a plurality of blood units and leukoreduced. The RBCs are separated according to type and group (i.e., ABO, Rh, etc.) and blood of the same blood type is collected (i.e, pooled) in a vat and treated via UV radiation and a type I and II quencher to remove any pathogen and inactivate residual WBCs. A storage solution of adenine, glucose, sodium phosphate, mannitol and guanosine is added following pathogen inactivation. The resultant cell containing composition is aliquotted into units comprising a uniform number of RBCs/mL. The units are stored at 1° C. to 6° C.

Example 2

Approximately 10 to 100 units of RBC are fractionated from a plurality of blood units and leukoreduced. The RBCs are separated according to type and group (i.e., ABO, Rh, etc.) and blood of the same blood type is collected (i.e, pooled) in a vat and treated using solvent/detergent methods to remove any pathogen and inactivate residual WBCs. A storage solution of adenine, glucose, sodium phosphate, mannitol and guanosine is added following pathogen inactivation. The resultant cell containing composition is aliquotted into units comprising a uniform number of RBCs/mL. The units are stored at 1° C. to 6° C.

Example 3

The cell containing composition from either of Examples 1 or 2 is analyzed for stability and viability of RBCs at a time period of 20 days, 40 days, 60 days and 100 days. Analysis of ATP and 2,3-DPG levels and percentage hemolysis is used to determine the stability and viability of the RBCs in the cell containing solution. Storage life of the cell containing composition is determined therefrom.

Example 4

About 100 units of blood are subjected to a process of leukoreduction with a leukoreduction filter and subsequently fractionated via centrifugation for about 20 min at 2000 rpm. The isolated RBCs from each unit are washed with a phosphate buffered saline and the blood type of each unit is tested. Blood units of the same type are then pooled. The pooled RBCs are further subjected to UV radiation for about 2-4 hours or to a solvent/detergent cleansing step to inactivate any pathogenic contaminants. A storage solution is added to the RBCs to produce a cell containing composition. The cell containing composition is gently agitated by mechanical means to maintain the RBCs uniformly dispersed in the storage solution. The cell containing solution is divided into units having a uniform number of RBCs/mL. The units are stored at about 1° C. to about 6° C. for about 50 to about 100 days prior to use.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A uniform dose red blood cell (RBC)-containing product obtained by the method comprising:
   a) separating an RBC component from a plurality of blood units, wherein either of the blood units or the RBC component has been leukoreduced to produce leukoreduced RBC components;
   b) pooling the leukoreduced RBC components from the plurality of blood units;
   c) treating the pooled RBC component to inactivate one or more pathogens;
   d) adding a storage solution to the pooled RBC component; and
   (e) dividing the pooled RBC component into a plurality of uniform dose units of RBC-containing product;
   wherein each unit of RBC-containing product comprises a uniform dose of RBCs; and wherein the RBC-containing product has a storage life of about 42 days to about 100 days.

2. The uniform dose RBC-containing product of claim 1, wherein the RBC-containing product is divided into a plurality of dosage units each comprising a uniform dose of RBCs before or after adding the storage solution.

3. The uniform dose RBC-containing product of claim 1, wherein the blood unit comprises a unit of whole blood or RBCs obtained by apheresis.

4. The uniform dose RBC-containing product of claim 1, wherein residual white blood cells in the pooled RBC component are inactivated.

5. The uniform dose RBC-containing product of claim 1, wherein each dosage unit of the RBC-containing product contains a uniform dose of RBCs, wherein the uniform dose is a uniform number of RBCs or a uniform amount of hemoglobin.

6. The uniform dose RBC-containing product of claim 5, wherein each dosage unit of the RBC-containing product contains about $1 \times 10^{12}$ to about $5 \times 10^{12}$ RBCs/unit.

7. The uniform dose RBC-containing product of claim 5, wherein each dosage unit of the RBC-containing product contains about 20-80 g of hemoglobin.

* * * * *